United States Patent [19]

Kaminski et al.

[11] Patent Number: 5,283,924
[45] Date of Patent: Feb. 8, 1994

[54] INTERDENTAL FOAM BRUSH AND TREATMENT GEL COMBINATION THEREWITH

[75] Inventors: John A. Kaminski, Newark, Calif.; Mingchih M. Tseng, Hingham, Mass.; Adrian Hart, Menlo Park, Calif.; Christopher H. Suhonen, Providencia Santiago, Chile; Robert G. Pitts, Half Moon Bay, Calif.

[73] Assignee: Gillette Canada, Inc., Kirkland, Canada

[21] Appl. No.: 29,843

[22] Filed: Mar. 11, 1993

Related U.S. Application Data

[63] Continuation-in-part of Ser. No. 893,479, Jun. 2, 1992, abandoned, which is a continuation-in-part of Ser. No. 724,129, Jul. 1, 1991, abandoned, which is a continuation-in-part of Ser. No. 586,067, Sep. 21, 1990, abandoned.

[51] Int. Cl.$^5$ .................... A61C 15/00; A46B 3/08
[52] U.S. Cl. .................... 15/244.1; 15/167.1; 15/176.1
[58] Field of Search ............. 15/244.1, 111, 22.1, 15/176.1, 167.1; 604/1

[56] References Cited

U.S. PATENT DOCUMENTS

| | | | |
|---|---|---|---|
| Re. 31,787 | 1/1985 | Chang | 424/52 |
| D. 291,504 | 8/1987 | Tarrson et al. | D4/104 |
| D. 291,505 | 8/1987 | Tarrson et al. | D4/104 |
| D. 293,858 | 1/1988 | Tarrson et al. | D4/104 |
| D. 298,182 | 10/1988 | Tarrson et al. | D4/104 |
| D. 303,043 | 8/1989 | Tarrson et al. | D4/104 |
| D. 304,785 | 11/1989 | Tarrson et al. | D4/104 |
| 982,232 | 1/1911 | Bartholomew | 15/244.1 |
| 1,631,133 | 6/1927 | Jones | 14/244.1 |
| 1,806,520 | 5/1931 | Cave | 15/206 |
| 2,206,542 | 7/1940 | Arnold | 15/106 |
| 2,218,738 | 10/1940 | Boysen | 15/244.1 |
| 2,319,841 | 5/1943 | Bate | 15/206 |
| 2,491,274 | 12/1949 | McNeill | 15/244.1 |

(List continued on next page.)

FOREIGN PATENT DOCUMENTS

| | | |
|---|---|---|
| 519804 | 3/1931 | Fed. Rep. of Germany . |
| 679174 | 7/1939 | Fed. Rep. of Germany . |
| 671738 | 3/1929 | France . |
| 167259 | 11/1974 | New Zealand . |
| 175697 | 4/1978 | New Zealand . |
| 218818 | 2/1988 | New Zealand . |

OTHER PUBLICATIONS

Dental Services; Austin H. Kutscher, DDS, School of Dental and Oral Surgery Columbia University, N.Y.; pp. 1886–1896 Chapter 105.

*Primary Examiner*—Philip R. Coe
*Assistant Examiner*—Patrick F. Brinson
*Attorney, Agent, or Firm*—Oblon, Spivak, McClelland, Maier & Neustadt

[57] ABSTRACT

An interdental foam brush with an elongate non-conductive, galvanic shock free stem having a boss, the stem having a brush support portion extending from the boss in the distal direction to a preferably rounded distal tip and a flexible handle engaging portion extending from the boss in the proximal direction. The brush support portion including its distal tip and the boss being enclosed in resilient, open-cell polymeric foam. The outer surface of the brush is tapered and converging in the distal direction. The boss is a stop means for limiting movement of the brush portion between interdental surfaces, and the brush support portion has a length approximating the width of a rear molar. The brush support portion has a diameter providing a brush support surface for effective cleaning while permitting passage of the brush between interdental surfaces. The foam has a hardness and pore density providing effective cleaning between interdental surfaces is achieved. Another aspect is a combination of the interdental foam brush described above and a handle. The interdental foam brush can be impregnated with a pharmaceutically effective amount of at least one agent for treating the gums or teeth in the form of a coating, solution, paste or gel.

18 Claims, 8 Drawing Sheets

U.S. PATENT DOCUMENTS

| | | | |
|---|---|---|---|
| 2,555,858 | 6/1951 | Oleksy | 15/244.1 |
| 3,018,778 | 1/1962 | Brilliant | 15/244.1 |
| 3,228,398 | 1/1966 | Leonard et al. | 15/244.1 |
| 3,429,963 | 2/1969 | Shedlovsky | 424/56 |
| 3,559,226 | 2/1971 | Burns | 15/167.1 |
| 3,720,975 | 3/1973 | Nelson | 15/167.1 |
| 3,724,018 | 4/1973 | Sills | 15/244.1 |
| 3,892,040 | 7/1975 | Marquis | 433/147 |
| 3,927,435 | 12/1975 | Moret et al. | 15/176 |
| 3,939,520 | 2/1976 | Axelsson | 15/167.1 |
| 3,956,480 | 5/1976 | Dichter et al. | 424/54 |
| 3,964,122 | 6/1976 | Kurdy | 15/184 |
| 4,030,199 | 6/1977 | Russell | 15/206 |
| 4,138,477 | 2/1979 | Gaffar | 424/52 |
| 4,150,457 | 4/1979 | Larson | 15/106 |
| 4,183,914 | 1/1980 | Gaffar et al. | 424/48 |
| 4,217,342 | 8/1980 | Gaffar et al. | 424/48 |
| 4,217,343 | 8/1980 | Gaffar et al. | 424/48 |
| 4,243,658 | 1/1981 | Chang | 424/52 |
| 4,296,096 | 10/1981 | Pierce | 424/52 |
| 4,304,766 | 12/1981 | Chang | 424/52 |
| 4,348,378 | 9/1982 | Kosti | 424/7 |
| 4,366,146 | 12/1982 | Chang | 424/52 |
| 4,387,479 | 6/1983 | Kigyos | 15/167.1 |
| 4,395,943 | 8/1983 | Brandli | 15/167.1 |
| 4,459,277 | 7/1984 | Kosti | 424/7.1 |
| 4,470,964 | 9/1984 | Chang | 424/52 |
| 4,485,090 | 11/1984 | Chang | 424/50 |
| 4,510,127 | 4/1985 | Chang | 424/52 |
| 4,537,765 | 8/1985 | Gaffar et al. | 424/53 |
| 4,576,190 | 3/1986 | Youssef | 132/89 |
| 4,590,064 | 5/1986 | Gaffar | 424/49 |
| 4,627,977 | 12/1986 | Gaffar et al. | 424/52 |
| 4,638,564 | 12/1986 | Youssef | 15/167.1 |
| 4,661,341 | 4/1987 | Benedict et al. | 424/48 |
| 4,691,404 | 9/1987 | Tarrson et al. | 15/167.1 |
| 4,780,923 | 11/1988 | Schuitheiss | 15/111 |
| 4,805,252 | 2/1989 | Tarrson et al. | 15/167.1 |
| 4,806,340 | 2/1989 | Gaffar et al. | 424/52 |
| 4,806,342 | 2/1989 | Gaffar et al. | 424/52 |
| 4,808,400 | 2/1989 | Gaffar et al. | 424/52 |
| 4,808,401 | 2/1989 | Gaffar et al. | 424/52 |
| 4,822,599 | 4/1989 | Mitra | 424/52 |
| 4,842,847 | 6/1989 | Amjad | 424/52 |
| 4,846,650 | 7/1989 | Benedict et al. | 424/55 |
| 4,847,070 | 7/1989 | Pyrz et al. | 424/52 |
| 4,869,898 | 9/1989 | Gaffar et al. | 424/52 |
| 4,871,531 | 10/1989 | Hartlaub et al. | 424/48 |
| 4,877,603 | 10/1989 | Degenhardt et al. | 424/57 |
| 4,880,619 | 11/1989 | Gaffar | 424/52 |
| 4,887,994 | 12/1989 | Bedford | 604/1 |
| 4,889,712 | 12/1989 | Gaffar et al. | 424/52 |
| 4,889,713 | 12/1989 | Gaffar et al. | 424/52 |
| 4,892,724 | 1/1990 | Amjad | 424/49 |
| 4,892,725 | 1/1990 | Amjad | 424/49 |
| 4,902,497 | 2/1990 | Crisanti et al. | 424/52 |
| 4,906,456 | 3/1990 | Gaffar et al. | 424/52 |
| 4,915,937 | 4/1990 | Amjad | 424/52 |
| 4,921,692 | 5/1990 | Gaffar et al. | 424/52 |
| 4,921,693 | 5/1990 | Gaffar et al. | 424/52 |
| 4,923,684 | 5/1990 | Imbrahim et al. | 424/52 |
| 4,925,654 | 5/1990 | Gaffar et al. | 424/52 |
| 4,931,273 | 6/1990 | Gaffar et al. | 424/52 |
| 4,960,586 | 10/1990 | Suhonen | 424/52 |
| 5,009,883 | 4/1991 | Suhonen | 424/52 |
| 5,029,358 | 7/1991 | Zimmerman | 15/167.1 |

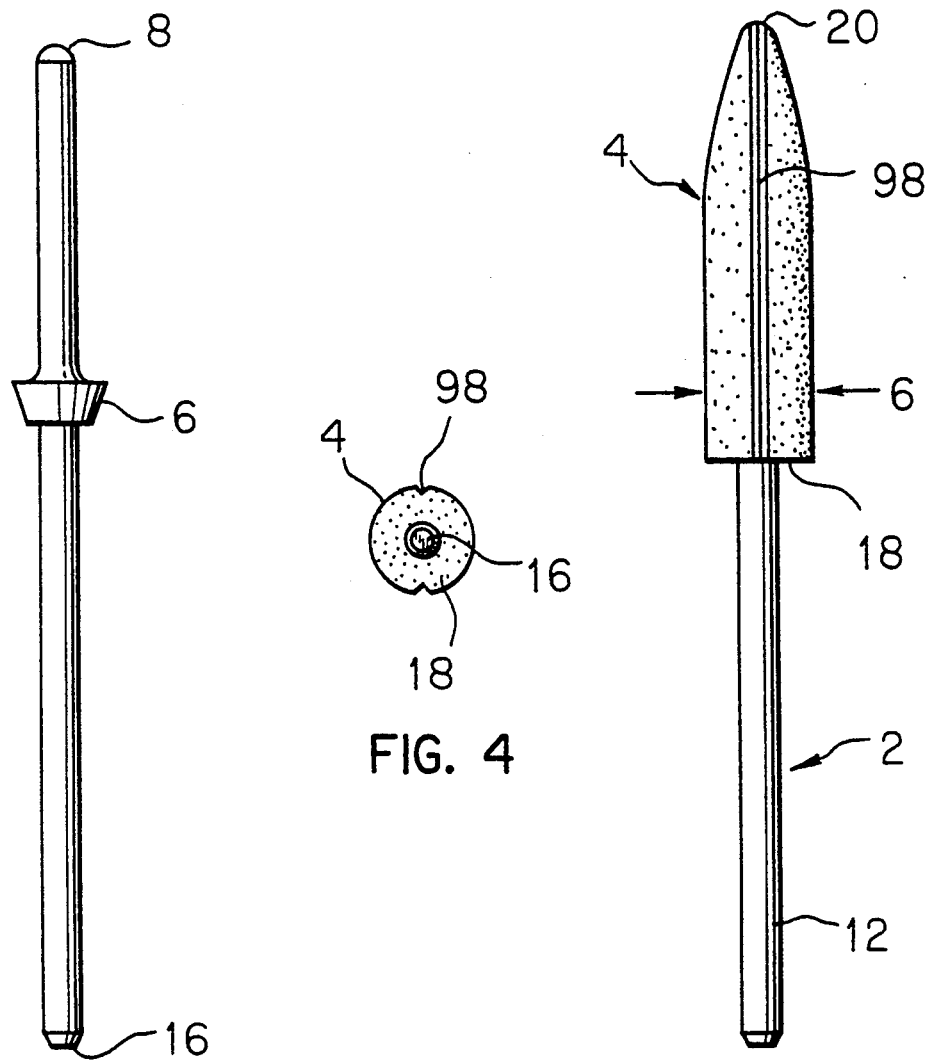
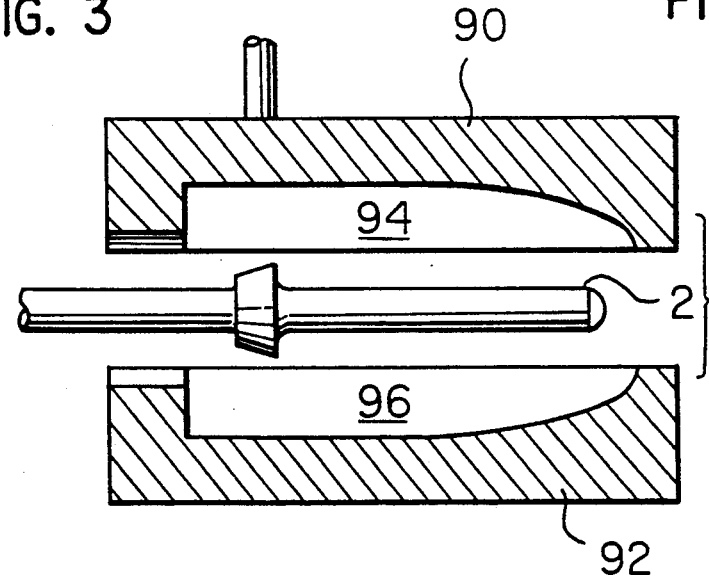

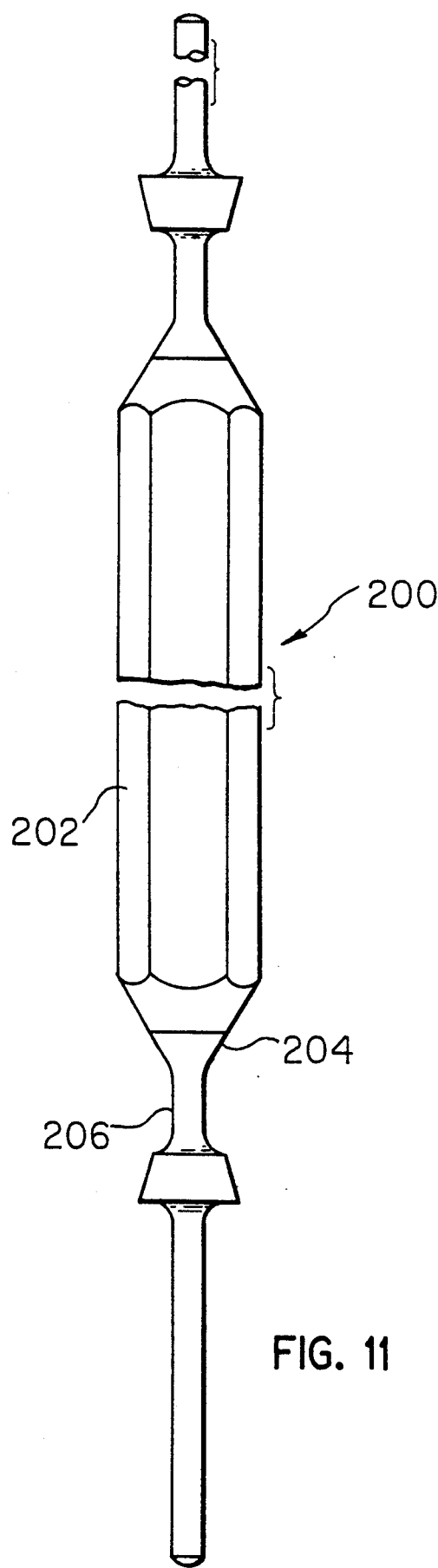
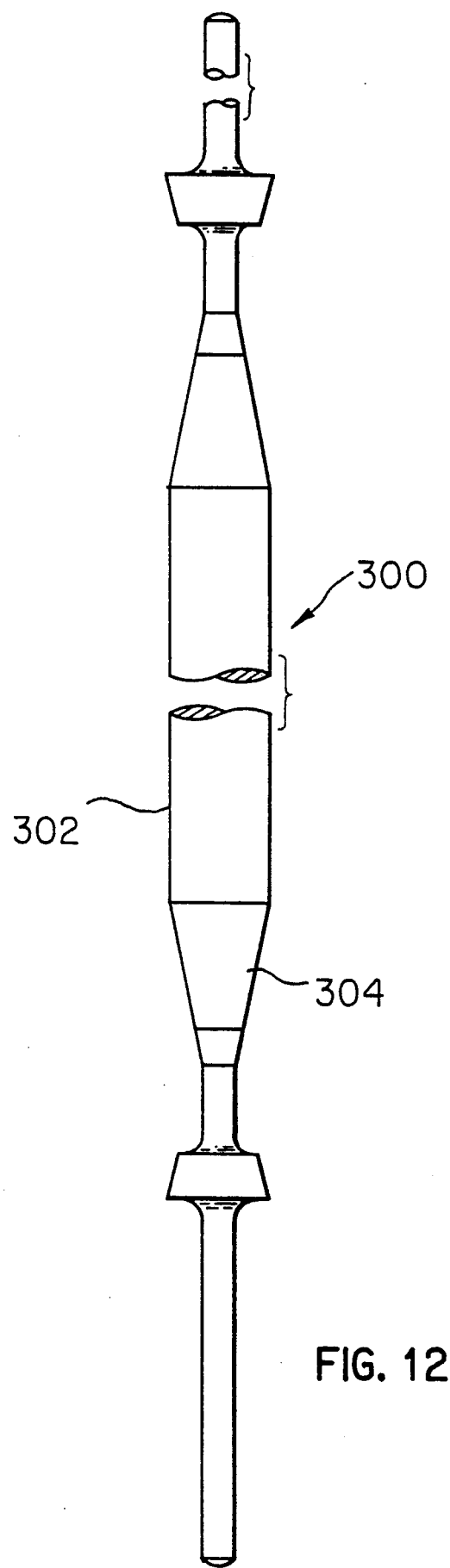
FIG. 11
FIG. 12

FIG. 13
FIG. 14
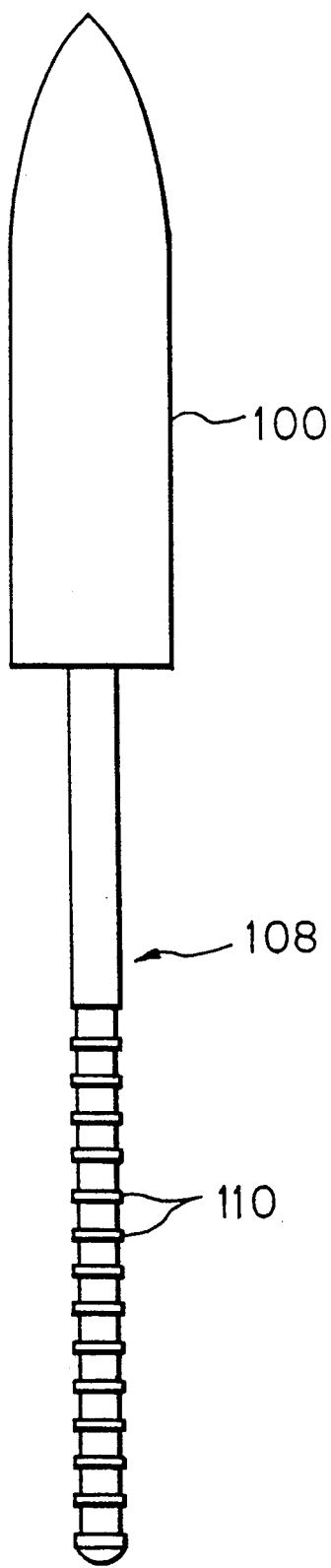
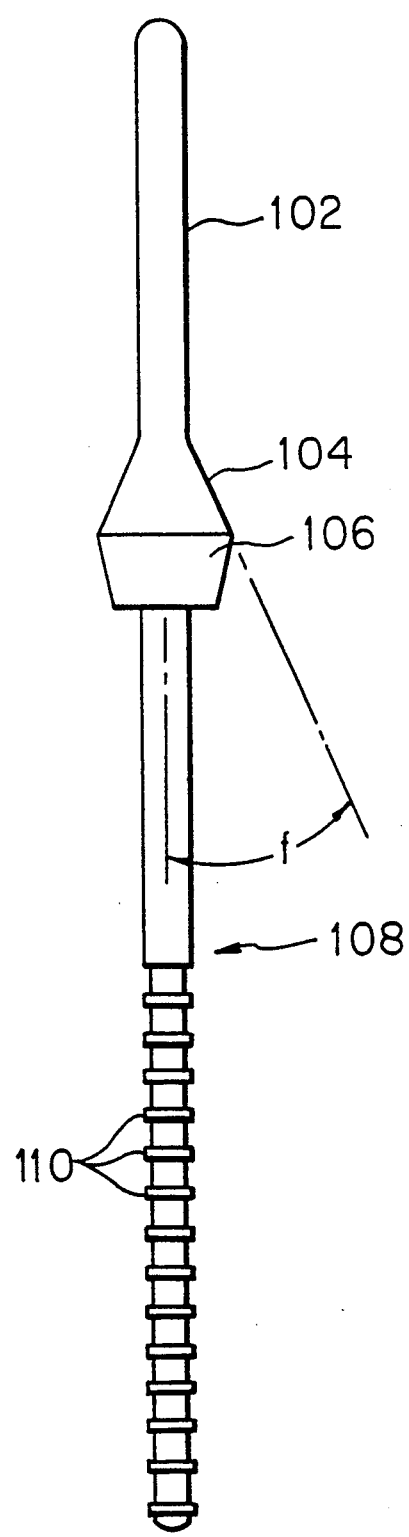

INTERDENTAL FOAM BRUSH AND TREATMENT GEL COMBINATION THEREWITH

RELATIONSHIP TO COPENDING APPLICATIONS

This application is a continuation-in-part of U.S application Ser. No. 07/893,479 filed Jun 2, 1992, and now abandoned, which is in turn, a continuation-in-part of U.S. patent application Ser. No. 07/724,129 filed Jul. 1, 1991 and now abandoned, which was, in turn, a continuation-in-part of U.S. patent application Ser. No. 07/586,067, filed Sep. 21, 1990 and now abandoned.

FIELD OF THE INVENTION

The present invention relates to interdental brush devices for oral care, and more particularly to a brush of the type in which a disposable brush element is securely retained on a handle by a pivotable cap member. This invention also relates to combinations of the interdental brush and treatment gels to be applied therewith to the teeth and gums.

BACKGROUND OF THE INVENTION

A great number of devices have been developed for oral prophylaxis of teeth and massaging of the gums. Typically, they comprise brushes which are retained on a handle by a removable cap member such as the pivotable cap shown in U.S. Pat. No. 4,780,923, the entire contents of which are incorporated by reference. In the conventional art such as Schultheiss, the brush is formed by nylon bristles captured between and extending radially from a pair of twisted metal wires which form a stem. The bristles are used to rub or wipe perpendicularly across the gum and tooth surfaces for cleaning the same. A commercial example of such a bristle brush is the interdental brush manufactured by Oral-B Laboratories of Redwood City, California, which is available in both a cylindrical and a tapered shape. Because the twisted wire is conductive and can produce a galvanic shock when contacting conductive restoration amalgams, an impervious coating of non-conductive material is required.

In the United States, most users become acquainted with interdental brushing after periodontal surgery. Most patients receive specific instructions on use after periodontal surgery, primarily to assure that surgical areas remain free of germs. Periodontists typically recommend oral prophylaxis using the existing nylon bristle brush. However, although such brushes satisfactorily perform their cleaning role, many patients are reluctant to use the brushes as instructed because of the pain produced by bristle tips scraping across tinder gum surfaces. A need therefore exists for an interdental brush which does not have bristles. Since electrical contact between wire stems and conductive restoration amalgams can be the source of galvanic shock, a need exists for a brush constructed entirely of materials which are not electrically conductive.

Previously known foam dental brushes have been designed for general oral prophylaxis of tooth surfaces, not interdental applications. Youssef (U.S. Pat. No. 4,628,564) describes a combination of a bristle toothbrush having a foam element on its tip for storing liquid. The device does not have the structure or dimensions permitting insertion into interdental passages.

Youssef (U.S. Pat. No. 4,579,190) describes a tapered foam brush mounted on a stem which can be impregnated with a chemical cleanser, producing a copious foam, and used for cleaning the outer tooth surfaces. The devices shown in this patent are not acceptable for cleaning interdental surfaces for several reasons. The rigid picks 14 and 20 and scrapper tip 22 (col. 3, line 55) do not conform to the interdental surfaces and are not effective for removing food and bacterial films from the gingiva and base of the teeth. Attempts to force the tapered foam element 10 into interdental surfaces are ineffective, since no firm structure is present.

We discovered that a tapered foam device mounted on a central support extending to its end to pull the form between tight spaces presents several serious problems which make it unsuitable for interdental use. Particularly in the molar areas at the rear of the mouth, interdental cleaning is awkward, and precise control of cleaning emblements is difficult. As shown in FIG. 1, the narrow tip of such as device is easily forced through the tooth surfaces to the other side and into contact with the adjoining cheek or tongue, producing trauma to these tissues. The foam which has been pulled through the interdental surface by the support then expands to form a shoulder surface opposed to the tooth, which like a barb, resists retraction. This frustrates vigorous reciprocal brushing action with such a device.

Application of medications to the teeth and gums is often required following periodontal surgery. A need therefore exists for an interdental brush treatment gel applicator to be used to apply needed medicaments to the teeth and gums.

SUMMARY OF THE INVENTION

It is an object of the present invention to provide an interdental foam brush which can be satisfactorily used for interdental cleaning, avoiding the need for cleaning bristles.

It is a further object of the present invention to provide a disposable interdental foam brush which can be securely and precisely positioned in a handle by a user and which is constructed entirely of non-conductive materials to eliminate the risk of galvanic shock.

It is a still further object of the present invention to provide an interdental foam brush which is shaped and supported to provide effective cleaning of interdental surfaces and to be vigorously applied between and retracted from interdental surfaces without bruising the tongue or inner mouth surface.

It is yet a further object of the invention to provide an interdental brush which is capable of retaining gels and medicaments for application to a user's mouth during brushing.

It is another object of the invention to provide a method of manufacturing an interdental brush having a brush member formed of an open cell foam material adhered onto an elongate stem.

The above, and other, objects are achieved according to the present invention by an interdental brush an elongate stem having a boss, the stem having a brush support portion extending from the boss in the distal direction to a preferably rounded distal tip and a flexible handle engaging portion extending from the boss in the proximal direction. The brush support portion including its distal tip and the boss are enclosed in resilient, open-cell polymeric foam. The outer surface of the brush is tapered and converging in the distal direction.

The boss is a stop means for limiting movement of the brush portion between interdental surfaces, and the brush support portion has a length of from 8 to 22 mm, whereby its extension between interdental surfaces is approximately limited to the width of a rear molar. The brush support portion has a diameter of from 1.5 to 3.3 mm, providing a brush support surface for effective cleaning while permitting passage of the brush between interdental surfaces.

The foam has a hardness of from 0.01 to 1 psi as measured by the Compression Force Deflection Test (ASTM D3574 Test C), and brush must be capable of providing a cleaning index not exceeding 2 as measured by the Wolfe Interproximal Plaque Index when used as directed, whereby more effective cleaning between interdental surfaces can be achieved.

The foam brush surface tapers or converges from an outer diameter of from 1 to 5 mm adjacent the boss to a respective outer diameter of from 0.1 to 1 mm adjacent said distal tip, whereby cleaning pressure is maintained in converging interproximal surfaces along the full with of the surfaces and barbless retraction of the brush from between interdental surfaces is obtained.

The boss is also a stop means for limiting movement of the handle engaging portion in a handle receptor.

Another aspect of this invention is a combination of the interdental foam brush described above and a handle, the handle having a grip portion and a handle end portion. The end portion of the handle has a transverse hole extending from a proximal end in a boss abutment surface of the handle to a distal end in a brush stem clamping surface. A cap is pivotly mounted on the handle end portion for movement from an unlocked position leaving the distal end of the transverse hole uncovered to a locked, brush stem clamping position covering the distal end of the transverse hole. The handle engaging portion of the elongate stem has a length exceeding the length of the transverse hole by an amount sufficient to allow secure engagement with the handle locking mechanism. The handle engaging portion of the elongate stem is positioned in the transverse hole, the boss portion thereof being positioned against the boss abutment surface. The cap has a stem engaging surface means for bending a brush stem extending from the transverse hole and clamping it against the brush stem clamping surface when the cap is pivoted from the unlocked position to the locked, brush stem clamping position.

Preferably, the foam material comprises a polyurethane having a pore density of from 20 to 120 PPI. The stem is preferably formed from a molded plastic such a polycarbonate, nylon, polyester or polyacetal.

One aspect of this invention is the combination of the interdental foam brush with a pharmaceutically effective amount of at least one agent for treating the gums or teeth in the form of a coating, solution, paste or gel.

For example, the brush can be impregnated with at least one agent for treating teeth or gums dispersed in a gel medium consisting essentially of water and an amount of a water dispersible gelling agent sufficient to form a gel. The treatment gel can contain from 0.05 to 5 wt. % of a soluble fluoride, for example. Alternatively, the treatment gel can have an acidic pH and contains pharmaceutically acceptable, treatment effective amounts of phosphoric acid and hydrofluoric acid.

According to a further feature of the invention, the brush may be made by placing the stem in a mold having a desired shape for the brush member, injecting a foam mixture into a mold to form the brushes, and cutting the stem to a desired length. The foam mixture may be a foamable hydrophilic polyurethane prepolymer (a derivative of toluene diisocyanate), a mixture of polyols and isocyanates, or a foamable elastomer. The stem must have a surface which will bond with the foam composition.

According to yet a further feature of the invention, the brush may be formed by a method including shaping layers of foam material and laminating two shaped layers of foam material onto a stem.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings.

FIG. 2 is a side view of the disposable interdental foam brush of FIG. 1.

FIG. 3 is a side view of the stem of the disposable interdental foam brush of FIG. 1.

FIG. 4 is an end view, as seen from the base of the stem, of the brush according to the embodiment of FIG. 1.

FIG. 10 is a schematic illustration of a step in a molding operation for producing the brush of FIG. 1.

FIG. 11 is a side view of a brush according to another embodiment of the invention.

FIG. 12 shows a variant of the embodiment of FIG. 11.

FIG. 13 is an improved interdental foam brush of this invention.

FIG. 14 is a view of the stem configuration of the interdental form brush shown in FIG. 13.

DETAILED DESCRIPTION OF THE PREFERRED EMBODIMENTS

Figure 1:
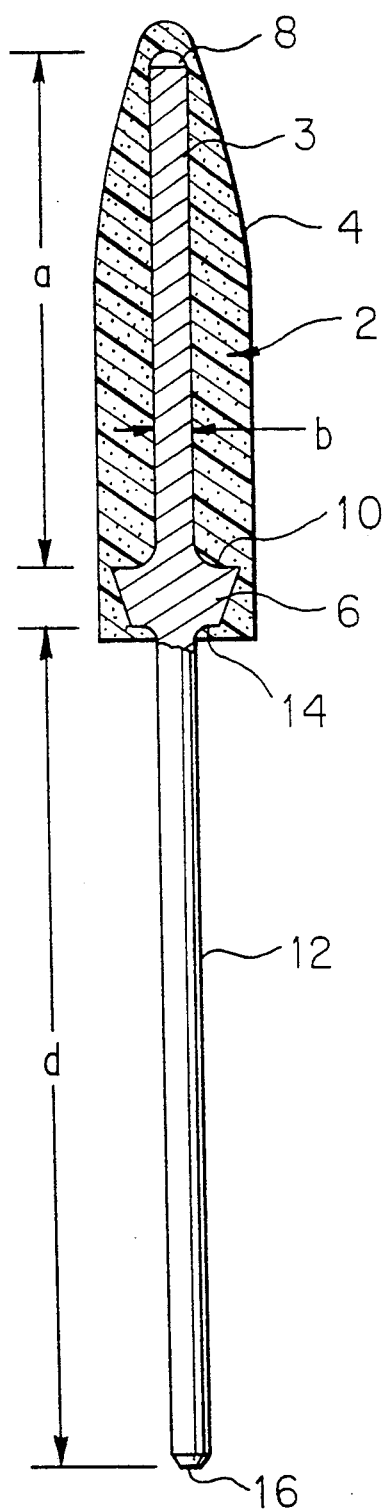
FIG. 1 is a cross-sectional view of a disposable interdental foam brush of this invention.

Preferred embodiments of the invention will now be described with reference to the accompanying drawings, in which the same reference numerals will be used to designate the same, or corresponding, elements throughout the several views.

FIG. 1 is a cross-sectional view of a disposable interdental foam brush of this invention. The elongate stem 2 has a brush support portion 3 extending from a boss or raised stop projection 6 to the distal tip 8. The distal tip 8 is preferably rounded or spherical to prevent penetration of the foam and trauma to gum surfaces during use. The boss stop surface 10 functions as a stop to limit movement of the stem tip 8 beyond the interdental surfaces of the molars as will be described in greater detail hereinafter and also to resist axial movement of the brush foam along the stem 2.

The length "a" of the brush support portion 3 of the stem 2 is selected to carry the foam brush completely through the interproximal spaces between the widest teeth, the rear molars, but not significantly beyond. The brush support portion thus preferably has a length "a" of from 8 to 22 mm and optimally from 13 to 20 mm, corresponding to the range of widths of rear molars.

The width "b" of the brush support portion of the stem 2 must be sufficiently large to provide the cross-sectional width required to provide firm support for the surrounding brush layer during its use in interdental cleaning but sufficiently small to allow insertion through interproximal spaces. The brush support portion thus preferably has a width "b" of from 1.5 to 3.3 mm, the width required to satisfy these functions.

The tapered foam brush 4 is adhered onto the stem 2 as shown in the cross-sectional view of FIG. 4.

Referring to FIG. 2 showing a side view of the disposable brush, the form brush 4 tapers from an outer diameter "c" of from 1 to 5 mm and preferably from 1.2 to 4 mm adjacent the boss 6 to the distal tip 8, whereby cleaning pressure is maintained in converging interproximal surfaces along the full width of the surfaces and barbless retraction of the brush from between the interproximal surfaces is insured. The brush width at the tip is sufficient to cover the tip of the stem and can be from 0.1 to 1 mm.

Referring to FIG. 1, the flexible handle portion 12 extends from the handle stop surface 14 of the boss 6 in the proximal direction toward the handle (described with respect to FIGS. 8-10 hereinafter) to proximal tip 16 and has a length "d" which is sufficient to functionally engage the handle and locking mechanism thereof.

The brush 4 is adhered to the stem 2, as shown in FIG. 1. The term "adhered", as used herein, is defined to connote that the foam be chemically or physically bonded to at least a portion of the stem surface so that the foam will remain in place on (not sliding along) the stem surface during use. Chemically inert or non-reactive smooth stem surfaces can be prepared to facilitate chemical and/or physical bonding with the foam by physical abrasion, treatment to provide chemically reactive groups on the surface, or combinations thereof. Surface treatments which increase chemical reactivity with polyurethane foams, for example, include treatments with corona discharge, chemical oxidants, and gas plasmas.

The brush 4 is formed of an open cell foam material, the open cell nature of the material assuring that the brush surface has cavities to receive and retain solids which are removed from gum, gingiva and tooth surfaces during rubbing application of the foam to these surfaces. The open cell structure allows the foam material to absorb water or other substances and completely dry after use. The foam preferably has a pore density of from 20 to 120 PPI and optimally has a pore density of from 40 to 80 PPI. The foam must have the softness required to prevent trauma to the gums and gingiva but the stiffness required to maintain pressure against the surfaces being cleaned and preferably has hardness of from 0.01 to 1 psi and optimally from 0.1 to 0.5 psi as measured by the Compression Force Deflection Test, ASTM D3574 Test C. A hardness within these ranges is selected to provide sufficient softness for conformation to tooth and gum surfaces and sufficient firmness to hold the brush surface against the tooth and gum surfaces with an effective cleaning pressure during the lateral cleaning motion with the brush.

A preferred material for the foam is polyurethane having a pore size and density of at least 80 PPI polyurethane, although smaller or larger cell sizes can be used depending upon whether an abrasive feel or a smooth feel is required, or larger or smaller surface cavities are required. Other possible foam materials include 10, 20, 30 or 60 PPI polyurethane or HZ polyethylene.

The foam brush must effectively remove organic material coating the interproximal tooth surfaces and accumulated in the gingiva. It must be capable of providing a cleaning index of not more than 2 and preferably less than 1 as measured by the Wolfe Interproximal Plaque Index described by Wolfe, G., *Journal of Clinical Periodontology*, 3:148-156 (1976).

As seen in FIGS. 2 and 4, the brush 4 has a base end 18 at a mid portion of the stem, which base end 18 is positioned closer to the proximal tip base end 16 of the stem than is the boss 6, so that the brush surrounds and covers the boss. The brush extends to a distal end 20 thereof which covers the distal leading end 8 of the stem. In the preferred embodiment, the brush is tapered and is substantially cone or bullet shaped. However, it may be appreciated that other shapes are possible, including cone shapes having circumferential corrugations, bullet shapes having circumferential corrugations, or any of the above shapes having longitudinal ribs.

The soft appearing foam will have greater aesthetic appeal to the user, who will therefore be less reluctant to use the brush as instructed to remove plaque from interproximal areas and below the gum line.

A further advantage of the open cell foam construction of the brush of the present invention is that it is possible to retain therein gels or other medicaments which are to be applied to the tooth and gum surfaces during use.

FIG. 3 is a side view of the elongate stem of the disposable interdental foam brush of FIG. 1. The stem 2 is formed of a plastic material and is preferably molded using a conventional injection molding process. The preferred material for the stem is Delrin (a DuPont trademark), although other materials can be used which provide stiffness with good flexibility. Alternative materials include polycarbonates, nylons, polyesters, or polyacetals.

The preferable polyacetal material is Delrin II, 500 grade.

Since the stem 2 and the brush 4 are both made of material which will not conduct electricity, the structure of this invention eliminates the risk of galvanic shock caused by contact with a conductive materials with a conductive restoration material such as a traditional silver amalgam.

As described above, the leading end 8 of the stem is preferably spherical with a diameter which is not greater than that of the stem. The base end proximal tip 16 of the stem 2 is preferably chamfered. The stem is formed with the annular boss 6 at a midportion thereof, i.e, positioned to be completely enclosed in the foam and positioned to be nearer the distal tip 8 thereof. The stem can have a substantially constant diameter between the leading end 8 and the boss 6, as shown in FIG. 1.

Figures 5, 7:
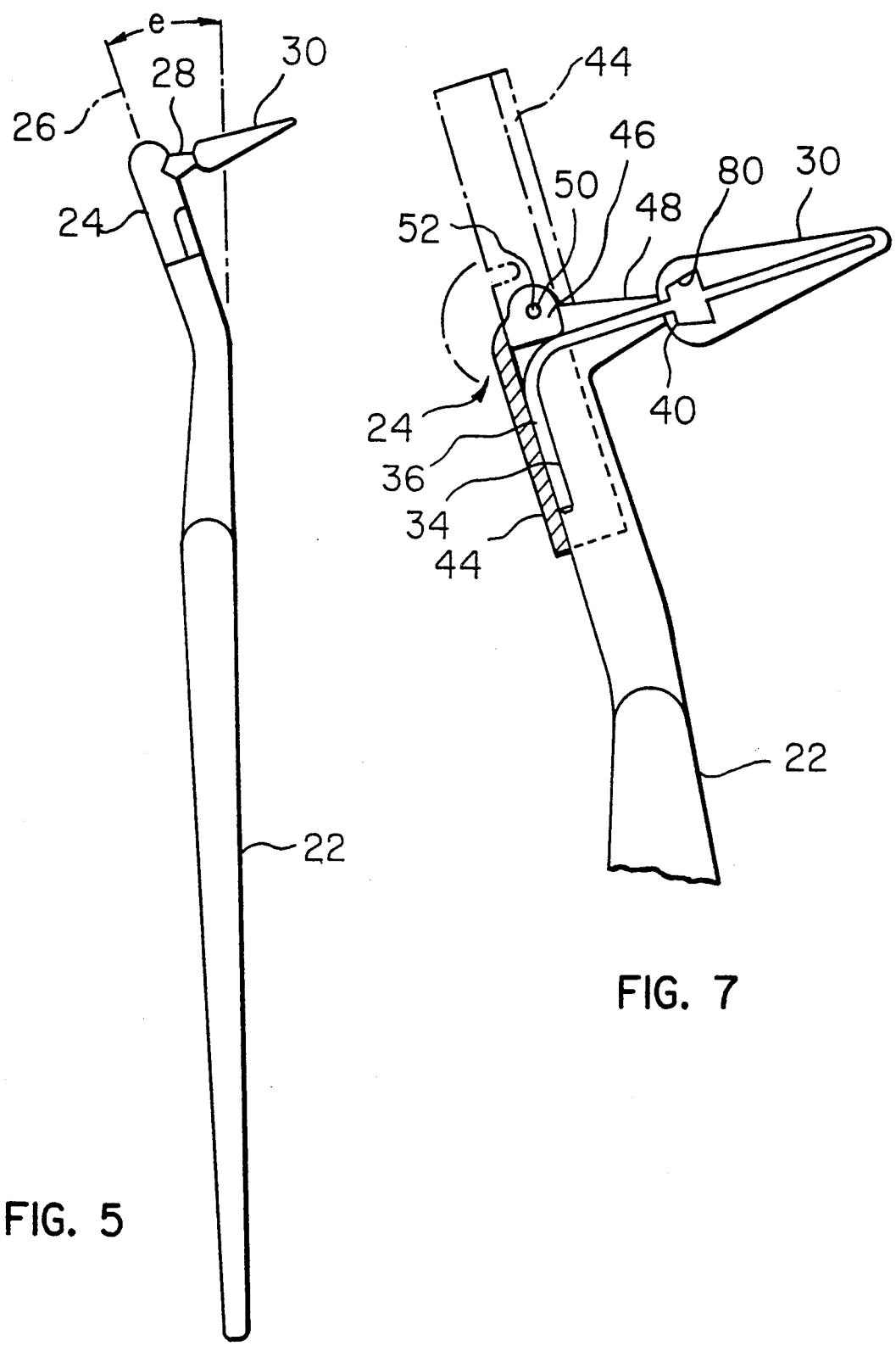
FIG. 5 is a side view of the interproximal handle and interdental foam brush combination of this invention.
FIG. 7 is a cross-sectional enlarged side view of the interproximal handle and interdental foam brush showing the locking mechanism for securing the brush stem in the handle.

FIG. 5 is a side view of the interproximal handle and interdental foam brush combination of this invention. The handle is of the type shown in U.S. Pat. No. 4,780,923, the entire contents of which are incorporated herein. The interproximal brush handle 22 terminates in end portion 24. Preferably, end portion 24 has a reduced thickness or diameter which is preferably bent at an angle "e" of from about 5° to about 25° with respect to the longitudinal axis 26 thereof. The tip 24 includes a tapered extension 28 and supports the interdental foam brush 30 of this invention.

Figure 6:
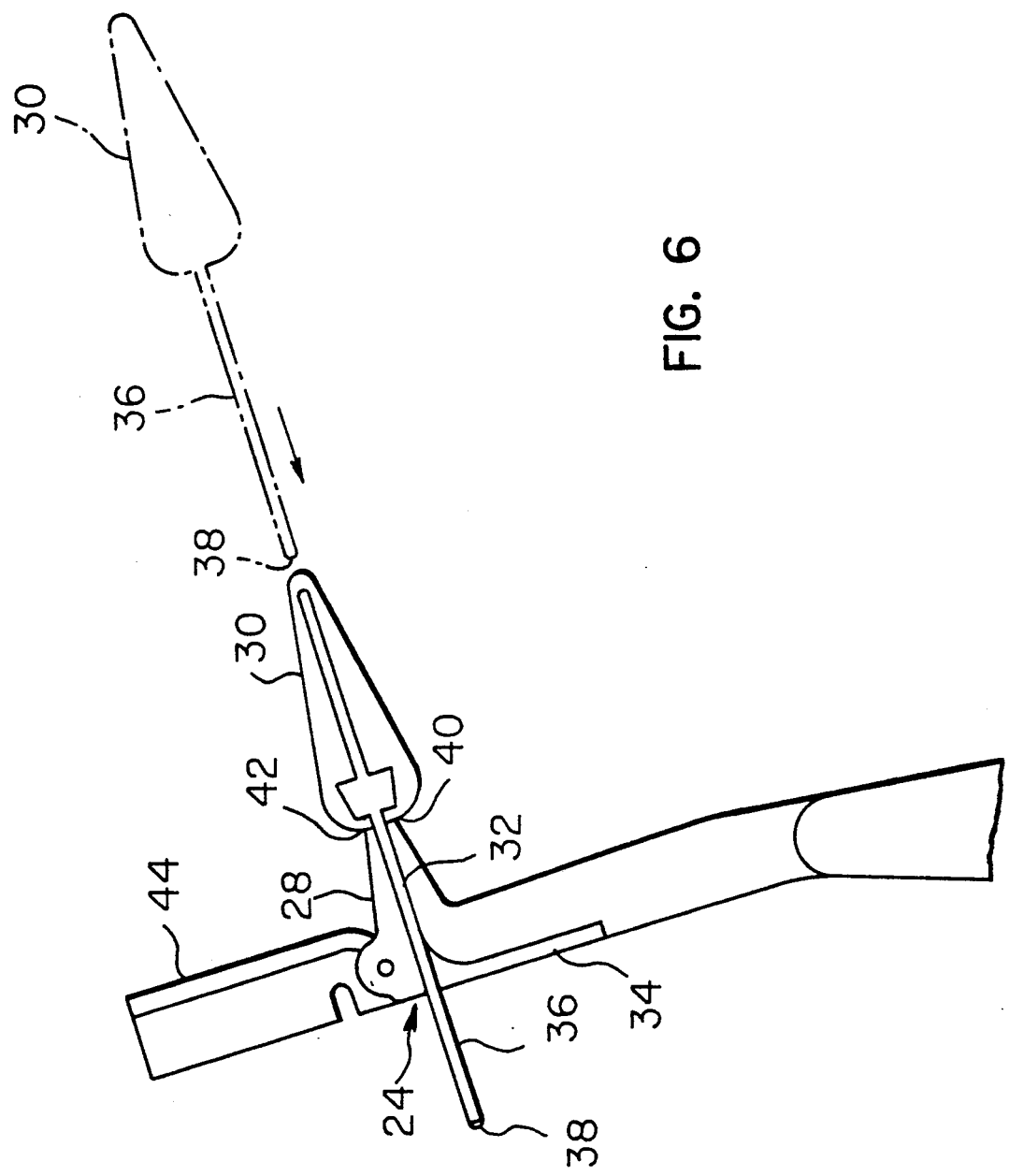
FIG. 6 is an enlarged view of the interproximal handle tip showing insertion an interdental foam brush therein.

FIG. 6 is an enlarged view of the interproximal handle tip showing insertion an interdental foam brush therein. A transverse hole 32 extends through the end 24 and tapered extension 28. On the back side, the transverse hole is connected with the longitudinal brush stem receptor groove 34. The diameter of the hole 32 is sufficiently large for easy insertion of the flexible interdental brush stem 36 but sufficiently small to secure the stem 36 against rotation and twisting when locked in place. The brush receptor groove 34 is sized to receive the brush stem 36 and retain it securely in place when the handle tip is locked.

The proximal tip 38 of the brush stem 36 is inserted in the transverse hole 32, and the stem is pushed through the hole 32 until the boss stop surface 40 of the brush (and it surrounding foam) is pressed firmly against the abutment surface 42 of the tapered extension 28. This stop precisely positions the brush portion without the need for approximate manual positioning in the handle.

FIG. 7 is a cross-sectional enlarged side view of the interproximal handle and interdental foam brush showing the locking mechanism for securing the brush stem in the handle. A molded polymeric cap 44 having opposed ears 46 which include holes 50 arranged and sized to accommodate a pivot pin 52 in the handle tip end 24 is pivotally mounted on the handle tip. When the disposable brush is firmly in place as described above, the pivotal movement of the cap 44 bends the stem portion 36 downward and presses it into the stem receptor groove 34, locking it in place.

Figure 8A:
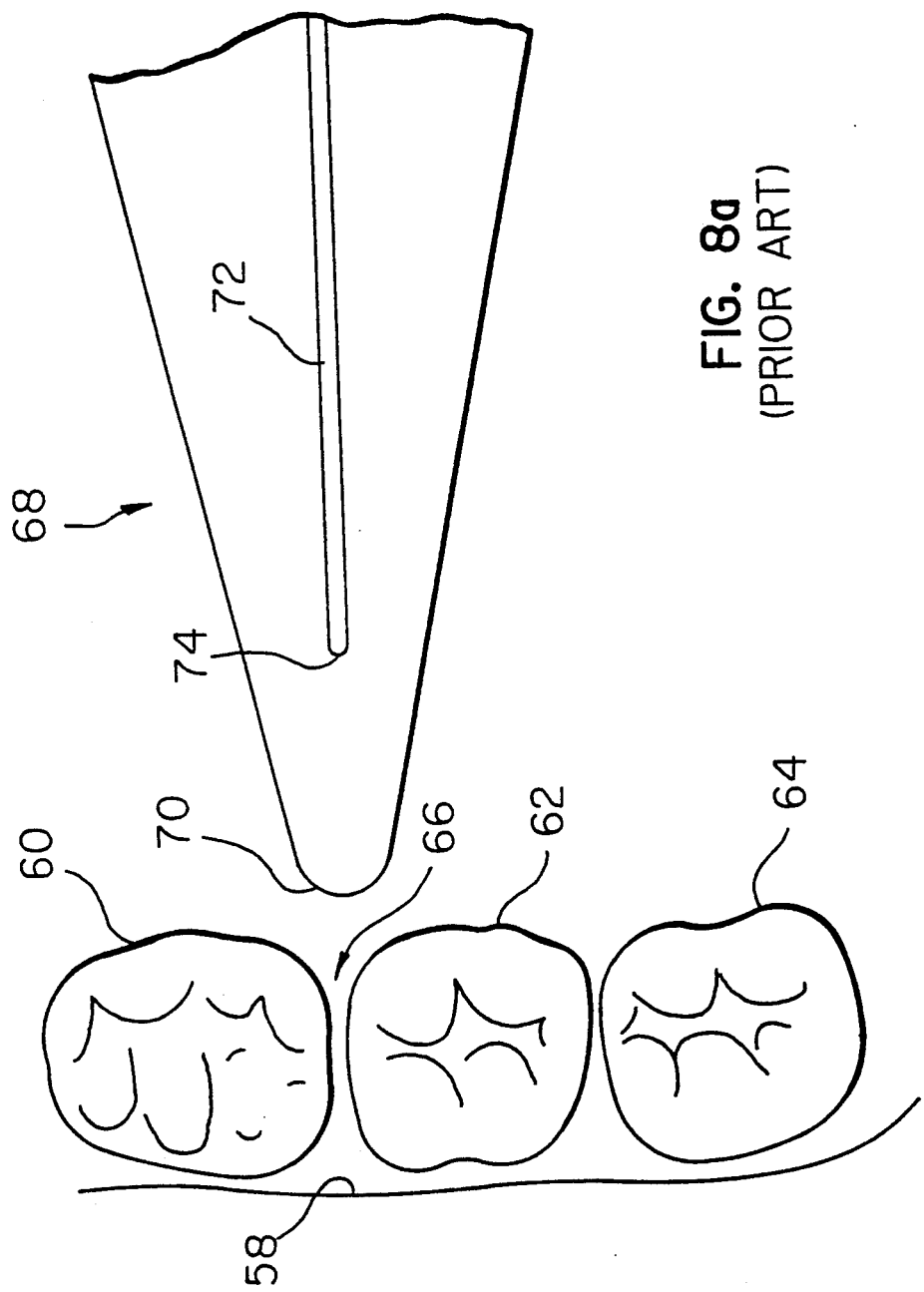
FIGS. 8a and 8b are schematic views of attempted and ineffective interdental application of a foam brush of the Prior Art.
Figure 8B:
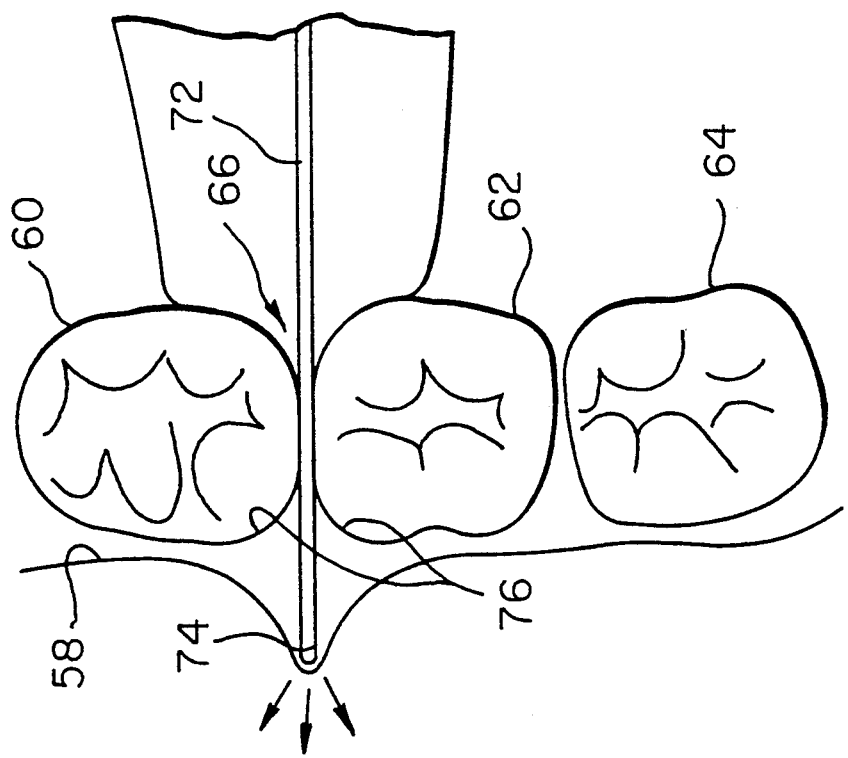

FIGS. 8a and 8b are schematic views of attempted and ineffective interdental application of a foam brush of the Prior Art for interproximal prophylaxis. U.S. Pat. No. 4,576,190 (FIGS. 2 and 3) shows a tooth brush comprising a tapered foam brush mounted on a thin stem. This large brush is designed to apply cleaning materials on the outer surface of teeth and scrub these outer surfaces with an electric toothbrush device. Interproximal cleaning of intermolar surfaces of the type effected by the foam brush of this invention would not be effective with this prior art brush for a number of reasons.

Referring to FIG. 8a, the mouth surface 58 presses against the rear molars 60, 62 and 64. The interproximal opening 66 is most easily approached from the inside. The prior art foam brush 68 has a soft, yielding tip 70 and a stem 72. The stem tip 74 is positioned at a substantial distance from the foam tip 72. This configuration is required for use of the brush to clean exterior tooth surfaces in the manner intended by the inventor thereof.

Referring to FIG. 8b, attempted insertion of the foam tip 70 through the interproximal passage 66 requires pushing the step tip 74 through the passageway. If the foam is sufficiently hard to be pushed ahead of the stem tip, it can be pressed through the opening 66, if at all, only by spreading the teeth.

If the foam tip is sufficiently soft to be enter the opening 66, it will not have the body required to be pushed ahead of the thin stem tip 74. A strong pressure will be required to press the stem tip through the opening in advance of the foam, the bulk of the foam material resisting the action. Under this large pressure in the rear of the mouth, sensitive and precise handling of the brush is not possible. Unavoidably, the stem tip will be forced through the opening 66 in advance of the bulk of the foam and into the mouth surface 58, producing trauma to the mouth surface. The soft foam pulled through the interproximal passage by the stem tip 74 will then expand, creating a barb shoulder 74 which will press strongly against the teeth and gums, seizing the brush, and resisting retraction of the brush through the passageway 66. The strong pressure required to complete its removal will continue after its sudden release, causing trauma to the tongue surface. Thus, attempted interproximal prophylaxis with such a brush will not only cause trauma to the opposed mouth surface but require a jerky, uncontrolled motion which would further irritate the highly sensitive surfaces of the gums following periodontal surgery. Prior art brushes of the type shown in this reference patent are thus totally unsuitable for effective cleaning of interproximal surfaces.

Figure 9:
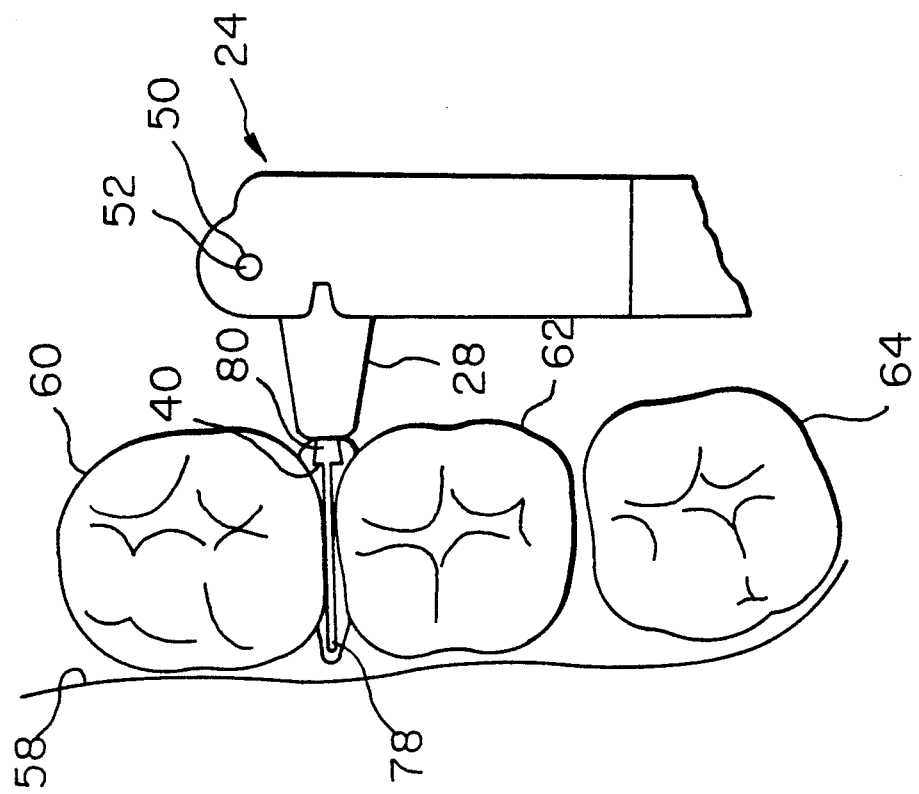
FIG. 9 is a schematic view of the highly effective interdental application of the form brush of this invention.

FIG. 9 is a schematic view of the highly effective interdental application of the form brush of this invention. The stem tip 78 of the foam brush 30 and the thin tapered foam layer adhered thereto are pushed easily through the interproximal spacing. The foam has a hardness required to press gently outwardly against the tooth and gum surfaces with sufficient pressure to effect a cleansing action during the reciprocal cleaning motion. The stop surface 40 (FIG. 7) of the boss 80 limits the penetration of brush tip 78 significantly beyond the interproximal passageway, thereby protecting the mouth surface 58 from trauma. Because of the tapered configuration of the foam, converging toward the tip 78, the mass of the foam passing through the passageway is not sufficient to create a barb shoulder, and the small force required to retract the brush is about the same as that required to push the brush into to the space being cleaned. A well controlled reciprocal motion can be achieved with gentle brushing and no trauma to the mouth and tongue surfaces adjacent to the area being cleaned. The foam brush dimensions and foam characteristics set forth hereinabove achieve these results.

The brush can be molded onto the stem in the manner shown in FIG. 10. There, a stem 2 having an extended base end is positioned between two mold halves 90 and 92, which are subsequently closed. The mold halves have recesses 94 and 96 which together define a mold volume having a shape corresponding to the desired shape of the brush. To form the brush, the foam material may be dispensed into mold cavities using a dispensing machine with distributing nozzles before the closing of the mold; or the foam material may be injected in a conventional manner following the closing of the mold. The base end of the stem precursor is then cut to appropriate length to form the stem.

Alternatively, the brush may be formed by two foam layers which are cut to the desired shape and laminated onto the stem. Lamination can be via a known adhesive, or by flame adhesion. In this case, the joint lines 98 of the two laminated halves will be visible as recesses.

Non-limiting dimensions for an optimum embodiment of the brush, in inches, are:
  stem length 1.163, stem diameter ("b") 0.035,
brush length 0.50,
maximum brush diameter ("c") 0.125,
boss axial length 0.050,
boss maximum diameter 0.10,
distance ("a") from leading end of stem to boss 0.39.

Another embodiment, which may be referred to as a "toothpick", is shown in FIG. 11. There, the stem is not clamped onto a separate handle for use. Instead, the stem 200 is radially enlarged at a central portion thereof to form a handle 202, so that the brush can be handled like a toothpick and used in a manner similar to a toothpick. In the embodiment of FIG. 11, the handle 202 of the stem 200 is hexagonal in section. The handle 202 terminates at conical ends 204 which taper at a 30° angle to merge with the smaller diameter portion 206. Portion 206 of the stem is identical to the part of the stem of the first embodiment which is covered by the brush member. Although not shown in FIG. 11, a brush member is adhered onto the portion 206 in the same way as described above.

As may be seen from FIG. 11, the opposite longitudinal ends of the stem 200 of this embodiment are identical, so that two brush members are formed at longitudinally opposite ends thereof. The ends may be alternated during use in the same way that one might alternate the ends of a toothpick.

The stem and foam brush portions preferably have the same configuration and dimensions described above with respect to the embodiment of FIGS. 1–4 designed for use with a handle. In a nonlimiting embodiment, the portion 206 of the stem has a diameter of 0.30 inches while the hexagonal handle 202 has a maximum diameter of 0.125 inches and the stem has an overall length of 2.75 inches.

The variant of FIG. 12 is identical to that of FIG. 11, except that the handle 302 of the stem 300 is circular and has conical ends 304 which taper at an angle of 15°.

FIG. 13 is an improved interdental foam brush of this invention, and FIG. 14 is a view of the stem configuration therefor. In this embodiment, the foam brush 100 is supported by a distal stem portion 102 leading from the stop surface 104 on boss 106. The stop surface 104 converges from the outer diameter the boss to the surface of the stem portion 102, forming an angle "f" of less than 45° with the axis of the stem to reduce the risk of trauma to gum surfaces. The proximal portion 108 of the stem has ribs or other irregularities 110 which prevent movement of the proximal portion when secured in the handle locking mechanism shown in FIG. 7.

The foam portion of the interdental brush of this invention can contain a medicament or treatment agent for treating teeth or gums in the form of a coating, gel, paste, solution or the like. The gel, paste or solution forms of treatment agent can be applied to the brush by the user. Preferably, the brush precoated or impregnated with medicament is provided to the dentist for application of medicament gels as a part of the dental treatment or to the patient for application subsequent thereto.

Medicament coatings, solutions, pastes and gels are well known and fully within the skill of the art. The preferred medicament vehicle is a gel medium. In general, the gels comprise an aqueous solution of the medicament and pharmaceutically acceptable, nontoxic additives such as aqueous gelling agents, humectants, surfactants, coloring or whitening agents, chlorophyll compounds, flavoring agents, preservatives, optional co-solvents, stabilizers, sweeteners, dyes, and pH modifying agents. Suitable materials and manufacturing processes are described in U.S. Pat. Nos. 4,418,057, 4,254,101, 4,627,977, 4,806,340, 4,847,070, 4,902,497, 4,906,456, and 4,960,586, for example, the entire contents of each of which are incorporated by reference.

Suitable medicaments include antimicrobial treatment agents. Suitable antimicrobial agents include, but are not limited to, quaternary ammonium compounds such as cetylpyridinium chloride, domiphen bromide, benzethonium chloride and the like; antibiotics and related drugs such as nitroimidazoles (metronidazole, etc.), tetracyclines, penicillins, clindamycin, spiramycin, nystatin, amphotericin, erythromycin, and the like; essential oils such as thymol, eucalyptol, menthol, methyl salicylate, and the like; metal salts such as mercurials, zinc salts, aluminum salts, and the like; other treatment compounds such as chlorhexidine, alexidine, hexetridine, IRGASAN DP300, salicylanilides, and the like.

Suitable flavors and fragrances include organic acids, esters, and aldehydes which are both safe and pleasant. Any suitable flavoring or sweetening material may also be employed. Examples of suitable flavoring constituents are flavoring oils, e.g. oil of spearmint, peppermint, wintergreen, sassafras, clove, save, eucalyptus, marjoram, cinnamon, lemon, orange and methyl salicylate. Suitable sweetening agents include sucrose, lactose, maltose, dextrose, levulose, sorbitol, xylitol, d-tryptophan, dihydrochalcones, sodium cyclamate, perillartine, APM (aspartyl phenyl alanine, methyl ester), saccharine and the like.

Biologically active materials which can be included in the gels are growth hormones and other compounds or compositions which enhance or stimulate tissue regrowth and healing.

Oxygenating agents which can be included in the gels include sodium perborate, urea peroxide, stabilized hydrogen peroxide, and the like.

Fluorides which can be included in the gels include sodium fluoride, stabilized stannous fluoride, amine fluorides and the like. A suitable stabilized stannous fluoride treatment gel is disclosed in U.S. Pat. Nos. 4,960,586 and 5,009,883, for example, the entire contents of which are hereby incorporated by reference. The fluoride can be provided in concentrations of from 0.05 to 5.0 weight percent.

Desensitizing agents which can be included in the gels include hydroxyapatite, formaldehyde, soluble oxalates, potassium salts including potassium fluoride, and the like.

Any other soluble, non-toxic pharmaceutically acceptable material which has a beneficial or therapeutic effect on the health, integrity or appearance of oral hard and soft tissues can be incorporated in the gels.

Any conventional humectant can be used. Suitable humectants include sorbitol, glycerin, or other edible polyhydric alcohols, the natural or synthetic gums conventionally used as hardening control agents and binders.

Suitable gelling agents for use in the composition of this invention include from 0.1 to 10 and preferably from 0.5 to 5 weight percent gelling agent. Gelling agents should be colloidal silica, magnesium aluminum silicate, and silicate free compounds such as Irish moss, gum karaya, gum arabic, gum tragacanth, xanthan gum, other polysaccharide gums, starch, polyvinylpyrrolidone, hydroxyethyl propylcellulose, hydroxybutyl methyl cellulose, hydroxypropyl methyl cellulose, hydroxyethyl cellulose, sodium carboxymethyl cellulose, other hydroxyvinyl polymers, and the like.

The compositions should have a pH within the range of from 2 to 11. One embodiment of a treatment gel for treating intact teeth has an acidic pH and contains hydrofluoric and phosphoric acids. A neutral treatment gel is preferred to treat teeth for which acid treatment is not suitable.

An optimum acidic gel can have the following approximate composition:

| Component | Amount, % w/w |
|---|---|
| Gelling agent | 2.5 |
| Glycerin | 5.0 |
| Aqueous Hydrofluoric Acid | 0.2 |
| Aqueous Phosphoric Acid | 1.5 |
| Sodium Fluoride | 2.6 |
| Sorbitol solution | 45.0 |
| Water | 41.0 |
| Xanthan Gum | 0.4 |

An optimum neutral gel can have the following composition:

| Component | Amount, % w/w |
|---|---|
| Gelling agent | 1.8 |
| Sodium Fluoride | 1.9 |
| Sodium Hydroxide Solution | 9.0 |
| Sorbitol Solution | 20.0 |
| Water | 65.2 |

This invention is further illustrated by the following specification but non-limiting examples of suitable gels which can be applied to the interdental foam brush of this invention.

EXAMPLE 1

Acidic Minute Treatment Gel

The following ingredients are combined to produce an acidic Minute Treatment Gel used for fluoride treatment of teeth.

| Component | Amount, % w/w |
|---|---|
| Carbopol[a] | 2.500 |
| FD&C Yellow #10 (1.0% aq. solution) | 0.085 |
| FD&C Blue #1 (1.0% aq. solution) | 0.025 |
| Glycerin 96% USP | 5.000 |
| Hydrofluoric Acid, 48% AR | 0.174 |
| Phosphoric Acid 75%, Food Grade | 1.490 |
| Prosweet Liquid[b] | 1.000 |
| Sodium Fluoride, USP | 2.599 |
| Sodium Saccharin USP Crystals | 0.210 |
| Sorbitol 70.0% Solution USP | 45.000 |
| Spearmint Oil NF, Extra | 0.600 |
| Titanium Dioxide USP | 0.010 |
| Water, Purified USP | 40.927 |
| Xanthan Gum[c] | 0.380 |

[a]CARBOMER 934P NF, carboxyvinyl polymer
[b]F&C International
[c]KELTROL, Kelco

EXAMPLE 2

The following ingredients are combined to produce an Neutral Treatment Gel used for fluoride treatment of teeth.

| Component | Amount, % w/v |
|---|---|
| Carbopol 934P[a] | 1.800 |
| FD&C Blue #1 (1.0% Solution) | 0.054 |
| FD&C Red #33 (1.0% Solution) | 0.123 |
| Grape Flavor #11540[b] | 0.500 |
| Methylparaben NF | 0.150 |
| Propylparaben NF | 0.050 |
| Prosweet Liquid[c] | 1.000 |
| Sodium Fluoride, USP | 1.870 |
| Sodium Hydroxide (10% Solution) | 9.000 |
| Sodium Saccharin USP Crystals | 0.210 |
| Sorbitol Solution 70% USP | 20.000 |
| Titanium Dioxide USP | 0.010 |
| Water, Purified USP | 65.233 |

[a]CARBOMER 934P NF, carboxyvinyl polymer
[b]Bush, Boake & Allen
[c]F&C International Obviously, numerous modifications and variations of the present invention are possible in light of the above teachings. It is therefore to be understood that within the scope of the appended claims, the invention may be practiced otherwise than as specifically described herein.

We claim:

1. An interdental foam brush comprising:
    an elongate stem having a boss, the stem having a brush support portion extending from the boss in the distal direction to a distal tip and a flexible handle engaging portion extending from the boss in the proximal direction,
    the brush support portion including its distal tip and the boss being enclosed in resilient, open-cell polymeric foam, the outer surface of the brush being tapered and converging in the distal direction,
    wherein the boss is a stop means for limiting movement of the brush portion beyond interdental surfaces, and the brush support portion has a length of from 8 to 22 mm, whereby its extension between interdental surfaces is approximately limited to the width of a rear molar, and a diameter of from 1.5 to 3.3 mm, providing a brush support surface for effective cleaning while permitting passage of the brush between inter dental surfaces.

2. An interdental foam brush of claim 1 wherein the foam has a compression hardness as measured by the Compression Force Deflection Test, ASTM D3574, Test C of from 0.01 to 1 psi.

3. An interdental foam brush of claim 1 which can provide a cleaning index not exceeding 2 as measured by the Wolfe Inter proximal Plaque Index, whereby more effective cleaning between interdental surfaces is achieved.

4. An interdental foam brush of claim 1 wherein the foam brush surface converges from an outer diameter of from 1 to 5 mm adjacent the boss to a diameter providing a thin covering on the distal tip, whereby cleaning pressure is maintained in converging interproximal surfaces along the full with of the surfaces and barbless retraction of the brush from between interdental surfaces is obtained.

5. An interdental foam brush of claim 1 wherein the boss is a stop means for limiting movement of the handle engaging portion in a handle receptor.

6. A combination of the interdental foam brush of claim 1 and a handle, the handle having a grip portion and a handle end portion, the end portion having a transverse hole extending from a proximal end in a boss abutment surface of the handle to a distal end in a brush stem clamping surface, a cap pivotly mounted on the handle end portion for movement from an unlocked position leaving the distal end of the transverse hole uncovered to a locked, brush stem clamping position covering the distal end of the transverse hole, the handle engaging portion of the elongate stem having a length exceeding the length of the transverse hole by an amount sufficient to permit secure engagement by the handle, and the handle engaging portion of the elongate stem being positioned in the transverse hole, the boss portion thereof being positioned against the boss abutment surface.

7. A combination of claim 6 wherein the cap has a stem engaging surface means for bending a brush stem extending from the transverse hole and clamping it against the brush stem clamping surface when the cap is pivoted from the unlocked position to the locked, brush stem clamping position.

8. An interdental brush of claim 1 wherein said foam material comprises a polyurethane having a pore density of from 20 to 120 PPI.

9. An interdental brush of claim 1 wherein said stem is formed of a molded electrically non-conductive plastic, whereby risk of galvanic shock by contact of the stem with a conductive tooth component is eliminated.

10. An interdental brush of claim 9 wherein said molded plastic is a member selected from the group consisting of polycarbonates, nylons, polyesters, and polyacetals.

11. An interdental brush of claim 1 wherein said distal tip is rounded.

12. An interdental brush of claim 1 in combination with a pharmaceutically effective amount of at least one agent for treating the gums or teeth in the form of a coating, solution, paste or gel.

13. An interdental brush of claim 12 wherein the brush is impregnated with at least one agent for treating teeth or gums dispersed in a gel medium consisting essentially of water and an amount of a water dispersible gelling agent sufficient to form a gel.

14. An interdental brush of claim 13 wherein the treatment gel contains from 0.05 to 5 wt. % of a soluble fluoride.

15. An interdental brush of claim 14 wherein the treatment gel has an acidic pH and contains pharmaceutically acceptable, treatment effective amounts of phosphoric acid and hydrofluoric acid.

16. An interdental brush of claim 15 wherein the treatment gel consists essentially of the following approximate composition:

| Component | Amount, % w/w |
| --- | --- |
| Gelling agent | 2.5 |
| Glycerin | 5.0 |
| Aqueous Hydrofluoric Acid | 0.2 |
| Aqueous Phosphoric Acid | 1.5 |
| Sodium Fluoride | 2.6 |
| Sorbitol solution | 45.0 |
| Water | 41.0 |
| Xanthan Gum | 0.4 |

17. An interdental brush of claim 14 wherein the treatment gel has a substantially neutral pH.

18. An interdental brush of claim 17 wherein the treatment gel consists essentially of the following approximate composition:

| Component | Amount, % w/w |
| --- | --- |
| Gelling agent | 1.8 |
| Sodium Fluoride | 1.9 |
| Sodium Hydroxide Solution | 9.0 |
| Sorbitol Solution | 20.0 |
| Water | 65.2 |

* * * * *